United States Patent [19]
Barnett et al.

[11] Patent Number: 5,494,674
[45] Date of Patent: * Feb. 27, 1996

[54] SKIN TREATMENT SYSTEM

[75] Inventors: Philip J. Barnett, Parkgate; Michael R. Lowry, Chester, both of United Kingdom

[73] Assignee: Elizabeth Arden Company, Division of Conopco, Inc., New York, N.Y.

[ * ] Notice: The portion of the term of this patent subsequent to Dec. 7, 2010, has been disclaimed.

[21] Appl. No.: 910,943

[22] Filed: Jul. 9, 1992

[30] Foreign Application Priority Data

Jul. 15, 1991 [GB] United Kingdom ............... 9115276

[51] Int. Cl.$^6$ ............................................. A61K 7/48
[52] U.S. Cl. ........................ 424/401; 514/63; 424/400
[58] Field of Search ................... 424/401, 405; 514/947, 629

[56] References Cited

U.S. PATENT DOCUMENTS 4,776,515  10/1988  Michalchik ........................... 239/3

FOREIGN PATENT DOCUMENTS

| 0029301 | 5/1981 | European Pat. Off. . |
|---|---|---|
| 0031649 | 7/1981 | European Pat. Off. . |
| 0132062 | 1/1985 | European Pat. Off. . |
| 0134951 | 3/1985 | European Pat. Off. . |
| 0163390 | 12/1985 | European Pat. Off. . |
| 0171184 | 2/1986 | European Pat. Off. . |
| 0224352 | 6/1987 | European Pat. Off. . |
| 0234842 | 9/1987 | European Pat. Off. . |
| 0253539 | 1/1988 | European Pat. Off. . |
| 0243031 | 7/1989 | European Pat. Off. . |
| 0368494 | 5/1990 | European Pat. Off. . |
| 0441501 | 8/1991 | European Pat. Off. . |
| 0468735 | 1/1992 | European Pat. Off. . |
| 0468736 | 1/1992 | European Pat. Off. . |
| 735161 | 11/1932 | France . |
| 108286 | 1/1899 | Germany . |
| 730363 | 1/1943 | Germany . |
| 56-97214 | 8/1981 | Japan ........................ A61K 7/13 |
| 1393333 | 5/1975 | United Kingdom . |
| 1569707 | 6/1980 | United Kingdom . |
| 2061769 | 5/1981 | United Kingdom . |
| 2073052 | 10/1981 | United Kingdom . |
| 2092025 | 8/1982 | United Kingdom . |
| 8500761 | 2/1985 | WIPO . |
| 90/00446 | 1/1990 | WIPO . |
| 90/03224 | 4/1990 | WIPO . |

Primary Examiner—Thurman K. Page
Assistant Examiner—Neil Levy
Attorney, Agent, or Firm—Milton L. Honig

[57] ABSTRACT

Skin treatment agents, such as those conventionally found in lotions or creams which are applied by gentle massage or rubbing-in with fingers, are delivered for example in substantially neat form by means of electrostatic spraying.

4 Claims, 1 Drawing Sheet of a skin treatment active with 100% and even coverage.

SKIN TREATMENT SYSTEM

FIELD OF THE INVENTION

The present invention relates to a system for delivering skin treatment agents directly to the skin. More particularly, the invention relates to methods and apparatus for applying such agents onto the skin using the principle of electrostatic spraying.

BACKGROUND OF THE INVENTION

Conventional skin treatment products are often liquid or viscous or semi-solid products, for example in the form of lotions or creams, and are traditionally applied by gentle massage or rubbing-in with the fingers. Because of the necessity for relatively large amounts of adjunct material, i.e. other than the one or more skin treatment actives which it is desired to deposit, to create an aesthetically acceptable product these known delivery systems are relatively elaborate, wasteful of cosmetic raw materials and have limited efficiency in delivering a desired active to an intended site. Control over applied dose is difficult and limited and the application of the product itself is often time consuming and messy.

As a further consequence of the presence in such products of significant amounts of stabilising ingredients such as surfactants, polymers, preservatives etc, sensory properties may often be poor, for example stickiness, greasiness and possibly irritation may be experienced by a user. This may be particularly pronounced where skin is damaged or diseased, in which circumstances application of a treatment agent by massage or rubbing-in will often be particularly undesirable.

The skin is in fact a very complex material and has many important characteristics which must be considered in the design of an optimised system for delivering cosmetic or therapeutic actives thereto. Skin has a multi-faceted surface having both lipophilic and lipophobic character, which for example allows the skin to "breathe" and release water vapour therefrom, yet function as an effective barrier against water, dirt and other unwanted materials. One particularly important physical feature of skin is its very rough surface terrain, which creates a problem in successfully applying a desired skin treatment active with 100% and even coverage.

In addition to the above described systems for delivering skin treatment agents, there are a small number of known examples where a skin treatment active is delivered using an aerosol spray. Two such examples are sprays for treating sunburn and sprains or other sports injuries. However, aerosol sprays, as are per se well known in the art for delivering personal products, also suffer from several disadvantages. For instance, the types of product and active agent which lend themselves to effective aerosol spraying are limited and the use of aerosols themselves still results in significant inefficiency and waste through non-target specific application and loss of active material to the atmosphere, which also results in unwanted atmospheric mists and possible contamination to the user's eyes, face or other body parts, which may present respiratory or other health problems. Aerosol spraying is also noisy and it is usually necessary to employ propellants which are frequently volatile organic compounds, which are now well recognised as being environmentally unfriendly, possibly hazardous to health and indeed are being legislated against in many countries of the world. The use of aerosols to deliver skin treatment agents is also believed to be even less efficient than conventional massage or rubbing-in delivery regimes in the context of percentage and evenness of coverage of the rough skin surface.

In a very different technical field, the principle of electrostatic spraying of liquid and solid materials is also known. In this technique a formulation to be sprayed is raised to a high electric potential in a spray nozzle to cause the formulation to atomise as a spray of electrically charged droplets. Such electrically charged droplets seek the closest earthed object to discharge their electric charge, and this can be arranged to be the desired spray target. Hitherto, electrostatic spraying techniques have been proposed principally for only large-scale industrial and agricultural applications, especially for delivering reactive materials like paints, adhesives and other surface coatings, as well as large-scale delivery of pesticides and other agricultural or agrochemical formulations. Examples of disclosures in this field include GB-A-1393333, GB-A-1569707, GB-A-2092025, EP-A-029301, EP-A-253539 and WO-A-85/00761, the contents of which disclosures are incorporated herein by reference.

More recently, there have been a small number of proposals for utilising the known principle of electrostatic spraying for delivering particular materials in specific applications other than those mentioned above.

EP-A-224352 suggests the use of an electrostatic sprayer for delivering a pharmaceutically active agent to the eye, to replace conventional ocular treatment using eye drops.

JP-A-56-97214 (dating from 1981) suggests the use of electrostatic spraying for applying a granular (i.e. solid particles of) colouring material to hair to effect surface coating thereof.

Also to be mentioned, though of less relevance, is U.S. Pat. No. 4776515, which proposes an electrodynamic fine particle negative ion generator adapted to spray various liquids, particularly water, but possibly also alcohol, perfume, ammonia, liquid medications and surfactants. The object of the disclosed system is to provide an ozone-free mist of negatively ionised liquid particles, (which presupposes that the material to be sprayed is ionizable), and the mist that is produced instantly disperses into an open area in which the apparatus is operated, e.g. a room, so that a far-reaching, uniform aerosol is generated which has particular applicability for large public areas such as hospitals, restaurants and offices. Clearly, this system is unsuitable for small-scale personal use and in many of its objects goes directly against the principles upon which a solution to the above mentioned prior art problems must be founded.

SUMMARY OF THE INVENTION

As a result of identifying and appreciating the above problems, prejudices and limitations of the known art and through much experimentation, we have now devised a system which enables the principle of electrostatic spraying to be put to effective use in delivering skin treatment agents directly to the skin, such that apparatuses and methods are now provided for such delivery regimes which are technically efficient, cost effective, safe, have widespread consumer applicability and appeal, and solve or at least ameliorate many, if not all, of the problems associated with the prior art.

Accordingly, in a first aspect the present invention provides a method of delivering a skin treatment agent directly to the skin, comprising electrostatically spraying the agent thereon.

In more detail, the method of this aspect of the invention preferably comprises:

(a) providing an apparatus which includes
  (i) a reservoir containing the skin treatment agent to be delivered which is an electrostatically sprayable form;
  (ii) at least one delivery means in communication with the reservoir;
  (iii) a high voltage generator powered from an electricity source; and
  (iv) control means for selectively applying the high voltage from the generator to the or each delivery means; and
(b) actuating the said control means to electrostatically spray the skin treatment agent from the or each delivery means directly onto the skin at an intended site.

In a second aspect, the present invention provides an apparatus for delivering a skin treatment agent directly to the skin, comprising:
(a) a reservoir for containing the skin treatment agent which is in an electrostatically sprayable form;
(b) at least one delivery means in communication with the reservoir;
(c) a high voltage generator powered from an electricity source;
(d) control means for selectively applying the high voltage from the generator to the or each delivery means to electrostatically spray the skin treatment agent from the or each delivery means.

In a third aspect, the present invention provides, in combination, the apparatus as defined above and an electrostatically sprayable composition consisting of or containing a skin treatment agent to be deposited directly onto the skin.

As a result of our investigations which have led to the present invention, we have further found that the use of electrostatic spraying for delivering skin treatment agents, as compared with the known application regimes, results in some unexpected and surprising findings as regards the effect on the profile of the skin terrain, which have been observed during surface profilometry studies. The unique effect of electrostatic spraying on the skin profile following product application indicates certain additional, unexpected advantages associated with this novel technique, particularly with respect to percentage and evenness of coverage of the skin surface during application. This aspect is discussed in detail further hereinbelow, with reference to the accompanying drawings.

DETAILED DESCRIPTION OF PREFERRED EMBODIMENTS

Figure 1A:
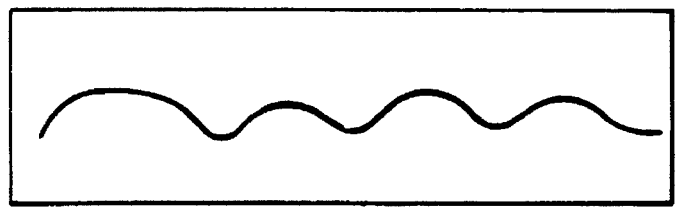
FIGS. 1(a) to 1(d) show schematically skin surface profiles of untreated skin and skin treated with treatment agents in regimes in accordance with the present invention and the prior art.

Having thus defined the main aspects of the present invention, preferred embodiments and various optional features and characteristics thereof will now be described in detail.

Skin treatment agents which may be delivered using the system of the present invention can be any of a very wide range of materials, preferably any of those skin treatment materials already known for use in conventional massage or rub-in lotions or cream products. Examples of such skin treatment agents are well known in the art and they may be delivered in accordance with the present invention either singly or in combination.

Examples of suitable skin treatment actives for delivery using the present invention include the following:

1. moisturisers, e.g. 2-hydroxyalkanoic acids, and acid-soap complexes thereof, polyols such as glycerol and glycols, 2-pyrrolidone-5-carboxylic acid, and other emollients or humectants;
2. occlusive materials, e.g. occlusive oils;
3. sun-protective materials, e.g. sunscreens, particularly UV-absorbing sunscreens;
4. after-sun care materials, e.g. materials for treating sunburn;
5. skin conditioning agents, e.g. agents which smooth or soften the skin;
6. skin colouring agents, e.g. artificial tanning products such as compositions containing dihydroxyacetone (DHA);
7. antibacterial or antifungal materials;
8. insect repellents;
9. astringent materials, e.g. hydrolisable tannins, phenolic acids associated with tannins, phenols associated with tannins, flavonoid compounds, natural extracts providing astringency, organic astringents and inorganic astringents (particularly salts of aluminium, zinc, iron (III), copper or silver);
10. skin cleansers and make-up or other cosmetic removers;
11. massage oils;
12. skin nutrients and healing agents;
13. spot and skin blemish treatment materials;
14. skin whiteners and agents for treating pigmentation disorders, e.g. freckles;
15. antiseptics and disinfectants;
16. anti-aging agents, e.g. for treating wrinkles or preventing development thereof;
17. agents for treating sensitive skin.

One particular advantage of the products which can be delivered by means of the present invention is that it is possible for at least some of, or even substantially all of, the adjunct components which hitherto have been necessary to include in skin treatment products to be omitted. Thus, it is possible for the required skin treatment active or actives to be delivered in neat or substantially neat form, or with only relatively minor amounts of adjunct materials. Any such auxiliary components, especially solvents or diluents and the like, may however still be used within the scope of this invention if desired or as necessary.

Indeed, for use in the present invention the skin treatment agent(s) is preferably provided in the form of a composition comprising one or more solvents or diluents which solubilise or are soluble in or miscible with the skin treatment active. Suitable solvents are well known in the art and include for example alcohols or polyols such as ethanol, isopropyl alcohol, propylene glycol, dipropylene glycol, phenyl ethyl alcohol, glycerol, 1,3-butanediol, 1,2-propanediol, isoprene glycol.

Compositions to be delivered using the present invention are preferably liquids. Any conventional adjunct materials which are present are preferably also liquid at room temperature, though may optionally be solids if used in minor amounts and do not deprive the composition of being electrostatically sprayable.

Generally there is the essential overall requirement of compositions useful in the present invention that they be electrostatically sprayable.

A principal characteristic of such electrostatically sprayable materials or compositions which it will usually be necessary to carefully select or adjust as necessary (as discussed further below), is their resistivity. Preferred resistivities fall within the range from about $10^4$ to about $10^{12}$ ohm cm, more preferably from about $10^6$ to about $10^{10}$ ohm cm. Resistivities of lower than $10^4$ may possibly be used. Resistivities of more than about $10^{12}$, e.g. up to about $10^{14}$ or more, may also be used, though such values are difficult to measure using cheap, conventional resistance measuring apparatus. Resistivity is measured using standard, conventional apparatus and methods, generally at 25° C.

Preferably compositions for delivery using the present invention are non-aqueous or may contain only a small amount of water, e.g. less than 10% by weight, preferably less than 5% by weight, even more preferably less than 1% by weight. This is because, due to its low resistivity, a predominantly aqueous composition is generally difficult to spray effectively using electrostatic means.

Generally compositions for application to the skin in accordance with the present invention will be leave-on compositions, so it will be Generally preferred to exclude from compositions for application any components which are disadvantageous in that respect and may impart deleterious effects on the skin when applied thereto and left on.

As mentioned above, depending upon the composition or material to be delivered, it may be necessary to adjust its resistivity by addition of one or more resistivity adjusting materials, examples and suitable amounts of which will be either known to persons skilled in the art, or readily derivable by simple experiment. Suitably, polar substances such as alcohols, e.g. ethanol, may be used to lower the resistivity of a Given material or composition, whereas non-polar substances, e.g. oils and other hydrophobic materials, may be used to increase its resistivity. Alternative resistivity adjusting materials include charged species such as salts, e.g. sodium chloride, or a salt conventionally used in buffers in personal products or pharmacological formulations.

In addition to resistivity, another parameter of the compositions to be sprayed which it may be necessary to carefully select and adjust is viscosity.

Materials of a wide range of viscosities may be suitable for use in the present invention, but suitably the viscosity is in the range of from about 0.1 to about 50000 mPas, more preferably from about 0.1 to about 10000 mPas, even more preferably from about 0.5 to about 5000 mPas (at 25° C.). If desired or as necessary one or more viscosity adjusting agents may be included. Examples of such agents include salts, e.g. alkali metal or ammonium halides, polymers and conventional thickening materials and oils and polar oil thickeners such as cosmetic oils, waxes, glycerides and suitable amphiphiles with melting points of from example >20° C.

Viscosity may in fact be used as a parameter to control the rate of delivery of the benefit or treatment agent to the intended site, if, as has been found with some embodiments of the system of the invention, it has a substantially inverse proportionality relationship with the flow rate of the material from the delivery means. For example, a particular delivery regime or a habit or need of a user may dictate an optimum delivery rate of the particular benefit or treatment agent being applied, in which case careful selection of the viscosity of the material to be sprayed can provide a self-regulating deposition mechanism.

For use in the present invention, the hardware and electrical componentry and circuitry may be of any suitable construction and design. The art of electrostatic spraying contains many examples of suitable apparatus which may be used in the present invention and such disclosures of such apparatus or particular features thereof may be applied either singly or in combination to the spray systems of the present invention.

Examples of suitable electrostatic spraying hardware include, in addition to those of the prior art references mentioned above, those of the following published references: GB-A-2061769, GB-A-2073052, EP-A-031649, EP-A-132062, EP-A-163390, EP-A-171184, EP-A-234842, EP-A-243031, EP-A-368494, EP-A-441501, EP-A-468735 and EP-A-468736; the disclosures of all of which are incorporated herein by reference.

As will be appreciated by persons skilled in the art, particular constructional features and design and electrical and other operating parameters of such apparatuses may be selected or adjusted as necessary, in the context of the present invention, in accordance with the desired functioning characteristics, as for example dictated by the composition or material to be sprayed and/or the needs or wishes of a user.

Features of the apparatus of the present invention which may be so selected and/or adjusted include for example: voltage generated by the high voltage generator and power source, electric field strength in or in the region of the product delivery means, flow rate of the product to be sprayed from the reservoir to and out of the delivery means, size and configuration of the delivery means itself and construction and properties of any product feed mechanism utilised between the reservoir and the output of the delivery means.

In preferred embodiments of the invention, preferred voltages generated by the high voltage generator from the power source are in the range of from about 2 to about 20 kilovolts, more preferably from about 5 to about 16 kilovolts. The most suitable voltage for a given system may depend upon the product to be sprayed, as well as other parameters, all of which will generally be selected to give an overall optimised system.

Electric field strengths which are responsible for the spraying action of the electrostatic apparatus will be largely dependent upon the voltage applied. However, field strengths may be controlled or adjusted if necessary, for example by changes in nozzle configuration or geometry and/or the use of field intensifying electrodes, which are well known in the art cited above.

Optimum flow rates of material to be sprayed will generally depend upon the composition of the product itself, e.g. upon the concentration of the active ingredient(s) being applied and may be selected appropriately on that basis preferably so as to avoid sensory negatives. Also, as already mentioned with respect to viscosity of the sprayable material, a suitable flow rate may be selected depending upon the particular delivery regime and/or habit or needs of a user. By way of example, preferred flow rates of compositions for delivery in accordance with embodiments of the invention are in the range of from about 0.00001 to about 0.5 ml/sec, more preferably from about 0.0001 to about 0.1 ml/sec, per delivery means.

The size and configuration of the one or more delivery means in the apparatus of the invention may be of any suitable form and again may be selected in association with other parameters to give an optimised functioning electrostatic spray delivery system. Commonly the or each delivery means will be in the form of a nozzle, preferably of insulating or semi-insulating material such as plastics or various polymers, as is well known in the art.

In one preferred form of nozzle, a conduit for carrying the product to be sprayed terminates in an orifice at the tip of the nozzle, from which orifice the product is ejected for example initially as a ligament but in any event eventually dispersing as a spray of charged droplets. The orifice preferably has a diameter of not greater than about 400 microns, more preferably not greater than about 350 microns. Even more preferably the orifice has a diameter of between about 125 and about 250 microns.

In an alternative preferred form the nozzle has a crown-like configuration at its tip and includes a narrow conduit through which the product is drawn to the tip under capillary action, as disclosed in EP-A-0243031, the disclosure of which is incorporated herein by reference. In this arrangement the electric field strength at the plurality of projecting portions of the nozzles is sufficiently large compared with the remaining edge areas of the nozzle to cause product to be electrostatically projected from the tip of the nozzle at each of those plurality of locations thereon.

The delivery means may advantageously include metering means to provide a dosing mechanism for delivering a predetermined fixed amount of material from the or each nozzle. Such an expedient may for example be useful in conjunction with a system having a controlled flow rate.

In preferred embodiments of the apparatus of the invention, the or each delivery means is in communication, i.e. preferably fluid communication, with the reservoir or reservoirs (if for example more than one material or composition is to be desired to be sprayed from the same apparatus or even the same delivery means) by virtue of product feed means.

In one preferred form, such feed means may comprise a wick, e.g. a porous wick, through and/or over which the product to be sprayed flows before reaching the point of high electric field strength where it is dispersed as a charged spray of droplets or particles. In another preferred form the feed means may comprise a hollow conduit through which the composition passes under the effect of capillary action. As a further alternative, in systems which for example require a particularly high flow rate, special feed means may be provided, for example a pump, which may usefully be employed with either of the other types of feed means described above. The pump may be of any suitable type, e.g. electrically operated, but more conveniently it may be a simple mechanical device which exerts pressure on the reservoir containing the composition to be sprayed, such that the composition therein is forced out of the reservoir to the delivery means.

As is well known in the art, the apparatus according to the invention preferably include a trigger (i.e. a manual control means) or alternatively an automatic control means to selectively apply the high voltage from the generator to the or each delivery means to electrostatically spray the benefit or treatment agent onto the hair and/or scalp. Any other suitable control means however, e.g. which automatically control actuation of the system, may be used, as will be appreciated by persons skilled in the art.

Skin surface profilometry studies

Skin surface profilometry was used to investigate the effects of applying liquid cosmetic compositions to skin in vivo, specifically to compare the effects of application regimes of the prior art (rub-in and pump spray) and of the present invention (electrostatic spray). Skin surface profilometry techniques and principles are described for example in the following two references, the disclosures of both of which are incorporated herein by reference:

1. "Topographies of dry skin, non-dry skin, and cosmetically treated dry skin as quantified by skin profilometry", T. H. Cook & T. J. Craft; J. Soc. Cosmet. Chem., 36, 143–152 (1985);
2. "Assessment of skin conditions using profilometry", Peter L Dorogi & Marek Zielmiski; Cosmetics & Toiletries, 104, (March 1989).

The following product application regimes were investigated:
(i) finger application/rub-in;
(ii) atomised droplets from a pump spray;
(iii) electrically charged droplets from an electrostatic spray.

Experimental

A silicone rubber impression material (SILFLO (TM), ex Flexico Developments Ltd.) was used to obtain negative replicas of the skin surface before and after product application. Replicas were taken from the volar forearm using a maximum of three sites per arm (each site 4×3 cm). The sites were separated by 2–3 cm and were a minimum of 4 cm distance from the wrist and the mid-arm fold. Each site was equilibrated for 15 min. at 21° C./50% relative humidity before replication.

A SURFCOM 113B profilometer from Advanced Metrology Systems Ltd. was used to characterise the replica surface. A stylus of 5 μm radius was made to traverse horizontally over a specimen surface with a stylus force of 0.4 g. The vertical movement of the stylus was measured and accumulated data was converted electronically to give standard roughness parameters. Measurements were made at 45 degree intervals of sample rotation and the mean of eight 10 mm long trackings were calculated.

Two parameters are reported:
$R_a$—the arithmetic mean of vertical variations from a calculated reference line (i.e. variation in peaks and valleys relative to a "mean reference line").
$R_{max}$—the maximum peak to valley height in the total scan.

Replicas taken before product application were used as controls. Products were applied at approximately 1 mg/cm² (normal skin product loading) and 11 mg/cm² (minimum dose from pump spray). Replicas were taken three minutes after product application. A single panellist was used and sequential treatments were separated by three days.

Two formulations were tested:
Product A: 65% DC344 (silicone oil ex Dow Corning) 5% ESTOL 1514 (iso propyl myristate ex Unichema) 30% Ethanol
Product B: a neat fragrance oil.

For the electrostatic spraying regimes in accordance with the invention, two different prototype apparatuses were used, in accordance with preferred embodiments of the invention, one giving a product flow rate of 2 g/min and the other a flow rate of 0.004 g/min. The electrical hardware and spraying parameters of the apparatuses were optimised to give fine, wide sprays in both cases. For the conventional atomised spray regimes, a conventional fine hairspray-type pump spray was used, such as that available from Cope Allman International Dispenser Group.

RESULTS

The results were as follows:

| Mean values and % change relative to control | | | | | |
|---|---|---|---|---|---|
| | | | $R_a$ (μm) | % change | $R_{max}$ (μm) | % change |
| (a) Low product loading (1 mg/cm²) | | | | | |
| Product A | Rub-in | Control | 13.8 | | 139.8 | |
| | | Treatment | 13.2 | −4 | 114.8 | −18 |

-continued

| | | | $R_a$ (μm) | % change | $R_{max}$ (μm) | % change |
|---|---|---|---|---|---|---|
| Product A | Electrostatic spray 1* | Control | 12.2 | | 124.8 | |
| | | Treatment | 15.8 | +30 | 159.2 | +28 |
| Product B | Rub-in | Control | 17.4 | | 212.6 | |
| | | Treatment | 13.4 | −23 | 136.8 | −36 |
| Product B | Electrostatic spray 2** | Control | 12.2 | | 171.6 | |
| | | Treatment | 12.8 | +5 | 148.4 | −14 |
| (b) High product loading (11 mg/cm²) | | | | | | |
| Product A | Pump spray | Control | 11.8 | | 112.6 | |
| | | Treatment | 14.6 | +24 | 185.2 | +64 |
| Product A | Electrostatic spray 1 | Control | 13.8 | | 142.0 | |
| | | Treatment | 14.0 | +1 | 156.6 | +10 |

*Flow rate 2 g/min
*Flow rate 0.004 g/min

CONCLUSIONS

The surface of skin exhibits a hierarchy of features involving furrows and micro-furrows as described in reference 2, mentioned above. The roughness parameters $R_a$ and $R_{max}$ provide a quantitative description of this complex surface.

Figure 1B:
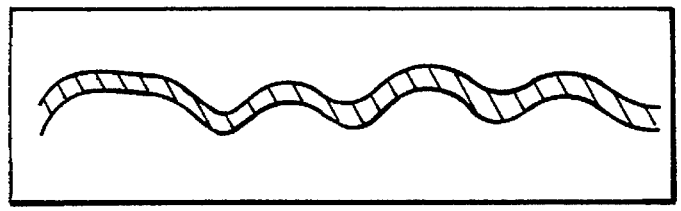
Figure 1C:
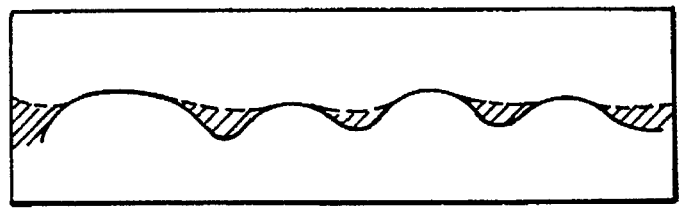
Figure 1D:
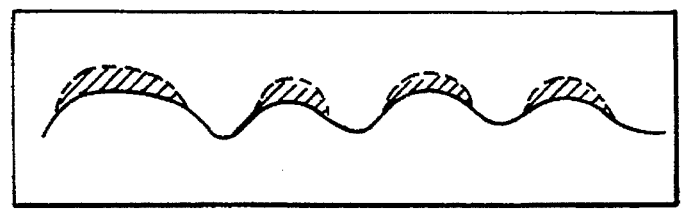

The effects on the roughness parameters of product deposition by various application regimes can be envisaged as falling into various categories, as illustrated by FIGS. 1(a) to (d) of the accompanying drawings, viz:

FIG. 1(a) represents an untreated skin surface, wherefrom control values for $R_a$ and $R_{max}$ are defined;

FIG. 1(b) represents even product coverage, with $R_a$ and $R_{max}$ undergoing little or no change;

FIG. 1(c) represents predominantly valley coverage, with $R_a$ and $R_{max}$ being significantly reduced;

FIG. 1(d) represents predominantly peak coverage, with $R_a$ and $R_{max}$ being significantly increased.

In the light of the above model, the reduction in $R_a$ and $R_{max}$ observed after applying product with finger/rub-in is consistent with the behaviour shown in FIG. 1(c), i.e. predominant filling of the valleys, leaving the peaks relatively uncovered.

The conventional pump spray, tested only at the high product loading, increased $R_a$ and $R_{max}$, indicating predominant peak cover (FIG. 1(d)).

The electrostatic applicators according to the invention produced a different response. At low product loading, product A increases $R_a$ and $R_{max}$, suggesting the behaviour shown in FIG. 1(d), i.e. predominant coverage of peaks. At the higher product loading, $R_a$ and $R_{max}$ were little affected, indicating coverage of both peaks and valleys, i.e. the behaviour shown in FIG. 1(b).

The above results support the finding that electrostatic application regimes as provided by the present invention can provide unique benefits over conventional application techniques for skin treatment products which require 100% and/or even coverage, for example especially where it is required to treat the skin for reasons of protection, conditioning or therapy.

Without intending to be bound by theory, the differences noted between the electrostatically sprayed products appear to reflect differences in product type (with respect to viscosity, wetting ability, volatility, for example) and delivery parameters (droplet velocity, charge, size, for example). The less volatile product B clearly gave relatively good cover even at low product loading, possibly because of higher product capture.

We claim:

1. A method for delivering a liquid skin treatment agent in a cosmetic composition directly to human skin to provide evenness of coverage on surfaces of the skin, comprising electrostatically spraying the agent directly thereon, the agent being electrostatically sprayable and being a silicone oil, said method further comprising:

(a) providing an apparatus suitable for small-scale personal use which includes
   (i) a reservoir containing the skin treatment agent to be delivered which is in an electrostatically sprayable form;
   (ii) at least one delivery means which is a nozzle in communication with the reservoir;
   (iii) a high voltage generator generating voltage in the range 2 to 20 kilovolts powered from an electricity source; and
   (iv) control means for selectively applying the high voltage from the generator to the at least one delivery means; and (b) actuating the said control means to electrostatically spray the skin treatment agent from the at least one delivery means directly onto the skin at an intended site.

2. A method according to claim 1, wherein the skin treatment agent is provided in the form of a composition comprising one or more solvents or diluents.

3. A method according to claim 1, wherein the skin treatment agent is provided in the form of a composition which has a resistivity in the range $10^4$ and $10^{12}$ ohm cm.

4. A method according to claim 1, wherein the skin treatment agent is in the form of a composition which is sprayed at a flow rate in the range 0.00001 to 0.5 ml/sec.

* * * * *

UNITED STATES PATENT AND TRADEMARK OFFICE
CERTIFICATE OF CORRECTION

PATENT NO. : 5,494,674 Page 1 of 1
APPLICATION NO. : 07/910943
DATED : February 27, 1996
INVENTOR(S) : Barnett and Lowry It is certified that error appears in the above-identified patent and that said Letters Patent is hereby corrected as shown below:

Title Page:

[ * ] Notice:

now reads: "The portion of the term of this patent subsequent to Dec. 7, 2010, has been disclaimed."

should read: -- The portion of the term of this patent subsequent to July 9, 2012 has been disclaimed.--

Signed and Sealed this

Twenty-seventh Day of February, 2007

JON W. DUDAS
*Director of the United States Patent and Trademark Office*